(12) United States Patent  
Beltrame et al.

(10) Patent No.: US 12,376,986 B2  
(45) Date of Patent: Aug. 5, 2025

(54) ANATOMICAL MENSTRUAL CUP

(71) Applicant: Luis Bernardo Beltrame, Prov. de Buenos Aires (AR)

(72) Inventors: Luis Bernardo Beltrame, Prov. de Buenos Aires (AR); Nicolás Antuña Barlocco, Prov. de Buenos Aires (AR); Eloy Martin Beltrame Molina, Prov. de Buenos Aires (AR)

(73) Assignee: Luis Bernardo Beltrame, Buenos Aires (AR)

( * ) Notice: Subject to any disclaimer, the term of this patent is extended or adjusted under 35 U.S.C. 154(b) by 434 days.

(21) Appl. No.: 18/007,611

(22) PCT Filed: Jun. 1, 2021

(86) PCT No.: PCT/IB2021/054804  
§ 371 (c)(1),  
(2) Date: Dec. 1, 2022

(87) PCT Pub. No.: WO2021/245554  
PCT Pub. Date: Dec. 9, 2021

(65) Prior Publication Data  
US 2023/0285180 A1    Sep. 14, 2023

Related U.S. Application Data

(60) Provisional application No. 63/034,070, filed on Jun. 3, 2020.

(51) Int. Cl.  
*A61F 5/455* (2006.01)  
*A61F 5/44* (2006.01)

(52) U.S. Cl.  
CPC .......... *A61F 5/4553* (2013.01); *A61F 5/4404* (2013.01); *A61F 5/455* (2013.01)

(58) Field of Classification Search  
CPC ....... A61F 5/4553; A61F 5/455; A61F 5/4404  
See application file for complete search history.

(56) References Cited

U.S. PATENT DOCUMENTS

| 679,478 A | 7/1901 | Lang | |
|---|---|---|---|
| 3,404,682 A * | 10/1968 | Waldron | A61F 13/26 128/838 |
| 3,626,942 A * | 12/1971 | Waldron | A61F 6/08 604/330 |

(Continued)

FOREIGN PATENT DOCUMENTS

| CN | 204971787 | 1/2016 |
|---|---|---|
| NL | 2021153 | 1/2020 |

OTHER PUBLICATIONS

International Search Report for PCT/IB2021/054804, mailed Nov. 16, 2021, 5 pages.

(Continued)

*Primary Examiner* — Guy K Townsend  
(74) *Attorney, Agent, or Firm* — NIXON & VANDERHYE

(57) ABSTRACT

Disclosed is an anatomical menstrual cup that has in its lower part a deformable hollow beak shape forming two symmetrical convex grip zones with respect to the X axis that passes through the center of the menstrual cup, where both grip zones contain a lip that allows to press, pull and rotate to facilitate manipulation of the menstrual cup.

20 Claims, 3 Drawing Sheets

(56) References Cited

U.S. PATENT DOCUMENTS

| | | | | |
|---|---|---|---|---|
| 3,845,766 | A | * | 11/1974 | Zoller .................... A61F 5/4553 D24/141 |
| 6,264,638 | B1 | | 7/2001 | Contente |
| 6,796,973 | B1 | * | 9/2004 | Contente .............. A61F 5/4553 128/832 |
| 10,016,308 | B2 | * | 7/2018 | Knox ................ A61F 13/00085 |
| D894,386 | S | * | 8/2020 | LeClerc ...................... D24/141 |
| D895,798 | S | * | 9/2020 | Newman ...................... D24/141 |
| D895,799 | S | * | 9/2020 | Newman ...................... D24/141 |
| 10,898,368 | B2 | * | 1/2021 | Medas .................. A61F 5/4553 |
| 10,959,873 | B2 | * | 3/2021 | Wilson ................. A61F 5/4553 |
| D923,785 | S | * | 6/2021 | Tsai ............................ D24/141 |
| 2008/0077097 | A1 | * | 3/2008 | Chambers ............. A61F 5/4553 604/330 |
| 2017/0189222 | A1 | * | 7/2017 | Lin ....................... A61F 5/4553 |
| 2018/0028350 | A1 | * | 2/2018 | Wilson ................. A61F 5/4553 |
| 2018/0214298 | A1 | * | 8/2018 | Medas ................. A61F 5/4553 |
| 2019/0282350 | A1 | * | 9/2019 | Conti ................. A61B 10/0045 |
| 2019/0314191 | A1 | * | 10/2019 | Bobarikin ............. A61F 5/4553 |
| 2020/0046572 | A1 | * | 2/2020 | Hwang ................. A61F 5/4404 |
| 2020/0060864 | A1 | * | 2/2020 | Font Caselles ....... A61F 5/4408 |
| 2020/0078208 | A1 | * | 3/2020 | Stoebe-Latham ..... A61F 5/4553 |
| 2020/0078209 | A1 | * | 3/2020 | Stoebe-Latham .......................... A61F 13/55105 |
| 2020/0214876 | A1 | * | 7/2020 | Tsai ....................... A61F 5/4553 |
| 2020/0375788 | A1 | * | 12/2020 | Zhang .................. A61F 5/4553 |
| 2021/0113363 | A1 | * | 4/2021 | Evans .................. A61F 5/4553 |
| 2022/0331146 | A1 | * | 10/2022 | Brush .................. A61F 5/4553 |
| 2022/0331147 | A1 | * | 10/2022 | Brush .................. A61F 5/4553 |
| 2022/0370238 | A1 | * | 11/2022 | Park ...................... A61F 5/455 |
| 2023/0285180 | A1 | * | 9/2023 | Beltrame .............. A61F 5/4553 |

OTHER PUBLICATIONS

Written Opinion of the ISA for PCT/IB2021/054804, mailed Nov. 16, 2021, 8 pages.

\* cited by examiner

Alternative 1

Alternative 2

ANATOMICAL MENSTRUAL CUP

This application is the U.S. national phase of International Application No. PCT/IB2021/054804 filed Jun. 1, 2021 which designated the U.S. and claims priority to U.S. Application No. 63/034,070 filed Jun. 3, 2020, the entire contents of each of which are hereby incorporated by reference.

FIELD OF THE INVENTION

The present invention refers to an anatomical menstrual cup that has in its lower part a deformable hollow beak shape forming two symmetrical convex grip zones with respect to the X axis that passes through the center of the menstrual cup, where both grip zones contain a lip that allows to press, pull and rotate to facilitate manipulation of the menstrual cup.

PRIOR ART

In the field of feminine intimate hygiene, there has been a considerable change in recent years. Compared to tampons or sanitary napkins, menstrual cups represent an adequate solution for the modern woman that is increasing due to its possible reuse, which allows reducing the waste produced, as is the case of tampons or sanitary napkins that must be discarded once they are used.

Devices similar to menstrual cups have been known, for example, since 1935. However, they do not meet the requirement of having an anatomical shape that allows them to be inserted and removed from the vagina properly. Among the documents where examples of menstrual cups are found, the following can be quoted:

U.S. Pat. No. 2,061,384 refers to a cylindrical catamenial receptacle with a protrusion for gripping that allows removal of the receptacle. This protrusion has a decrease in section at the junction with the catamenial receptacle; therefore, it has the drawback that during extraction this zone with reduced section has high chances of breaking, reducing the useful life of the catamenial receptacle.

U.S. Pat. No. 2,616,426 presents a catamenial trap that has a shape that is not very anatomical, without grip zones, which does not allow easy insertion and removal of the catamenial trap in the vagina.

U.S. Pat. No. 8,795,248 refers to a device and method for collecting menstrual blood that uses a receptacle in the shape of a hemisphere of a comprehensible material for the collection of menstrual fluid, said device is not completely anatomical in shape and has a gripping ring that allows its removal from the vagina. However, this ring constitutes a zone with a decreased section of the material that composes it, and therefore, has high chances of breaking, reducing the useful life of said device.

U.S. Pat. No. 10,898,368 corresponds to an ergonomic menstrual cup having a flared bottom portion that includes a plurality of non-convex gripping surfaces substantially axisymmetrically distributed on said flared bottom portion and which are configured to be squeezable between the fingers to facilitate removal of the menstrual cup. This document corresponds to the closest prior art. However, the present inventors found improvements leading to a new anatomical menstrual cup that offers better removal of the menstrual cup and greater comfort for the woman who uses it.

SUMMARY OF THE INVENTION

The present invention refers to an anatomical menstrual cup (10) comprising a lower part (11) and an upper part (22) separated by a horizontal Y axis (21), where the lower part (11) results from the intersection of an elliptic paraboloid of revolution with two symmetrical convex surfaces (13, 14) around a vertical X axis (20), with a rounded beak-shaped protrusion (12). Said protrusion guarantees comfort during use. The symmetrical convex surfaces (13, 14) represent two grip zones, which facilitate the insertion and removal of the menstrual cup in the user's vagina. In the previous anatomical menstrual cup (10), each of the two symmetrical convex grip zones (13, 14) has a lip (15, 16) that allows it to be pinched with the user's fingers to facilitate the extraction of said anatomical menstrual cup (10).

In the previous anatomical menstrual cup (10), the upper part of the grip zones (13, 14) is below the middle of the anatomical menstrual cup (10), that is, below the horizontal Y axis (21) or the upper part of the grip zones (13, 14) barely exceeds the middle of the anatomical menstrual cup (10), that is to say barely exceeds the horizontal Y axis (21).

In a variant of the previous anatomical menstrual cup (10), the upper part of the grip zones (13, 14) is below the middle of the anatomical menstrual cup (10), that is, below the horizontal Y axis (21) in a distance approximately equal to the thickness of the wall that makes up the anatomical menstrual cup (10).

In another variant of the anatomical menstrual cup (10), the upper part of the grip zones (13, 14) barely exceeds the middle of the anatomical menstrual cup (10), that is, it barely exceeds the horizontal Y axis (21) in a distance approximately equal to the thickness of the wall that makes up the anatomical menstrual cup (10).

The anatomical menstrual cup (10) according to any of the previous variants contains an upper ring (18) at the beginning of the upper part (22) that allows the cup to seal against the vaginal walls of the user in order to avoid the loss of vaginal discharge when in use.

The anatomical menstrual cup (10) according to any of the previous variants has an upper ring (18) that is not perpendicular to the vertical X axis (20) but forms an angle δ which is within the range of 95° and 111°.

In the anatomical menstrual cup (10) according to the previous variant, under the upper ring (18) in the upper part (22), there are at least two holes (19) that allow the passage of air when the menstrual cup (10) from the user's vagina. These holes have an irregular shape, other than a circumference.

BRIEF DESCRIPTION OF THE DRAWINGS

For a better understanding of this description, a series of illustrations are attached where its main components are outlined.

DETAILED DESCRIPTION OF THE INVENTION

Figure 1:
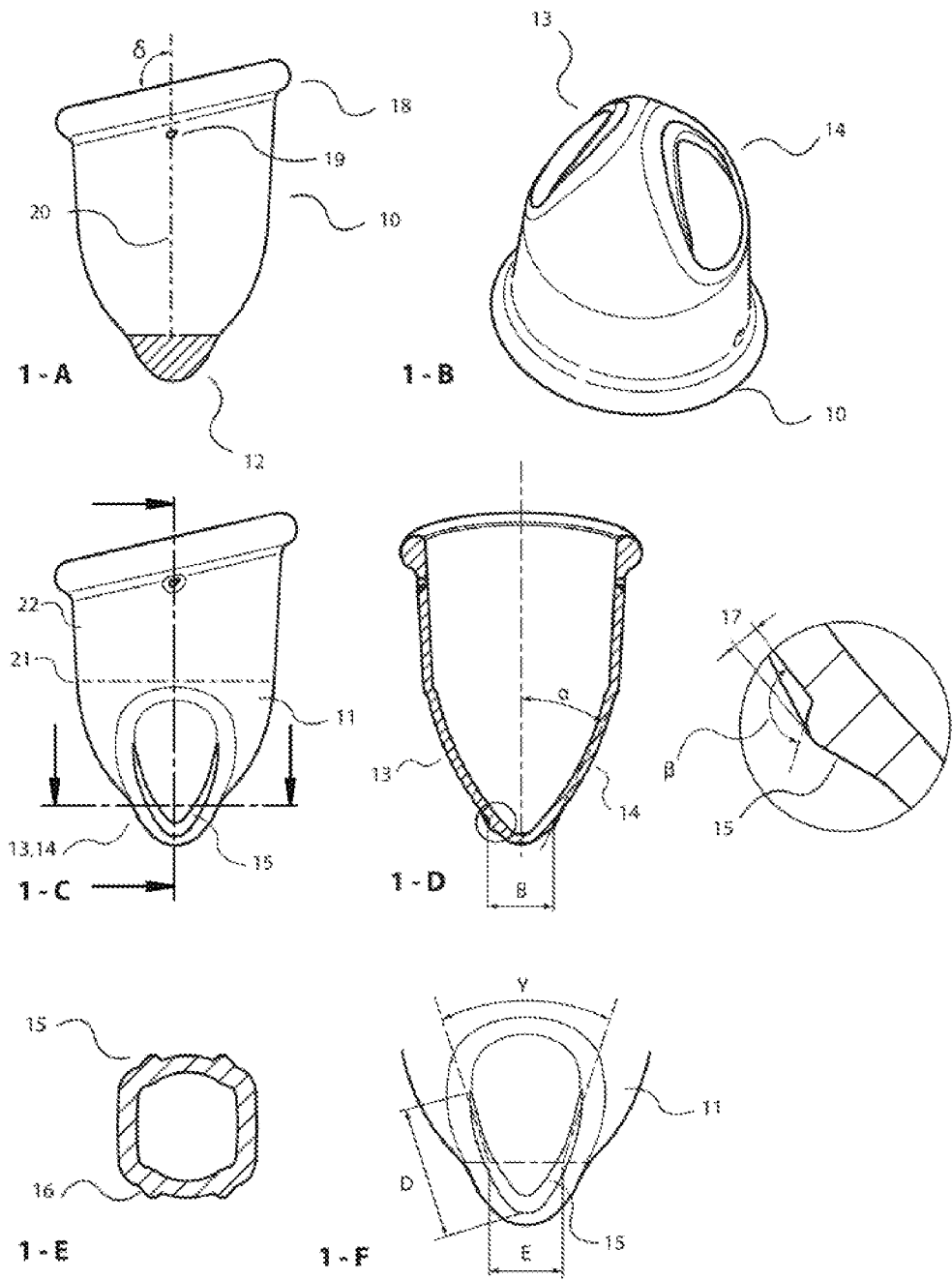
FIG. 1: Shows a detailed alternative of the anatomical menstrual cup of the invention where the upper part of the grip zones (13, 14) is located below the middle of the anatomical menstrual cup; in 1-A the side view is shown where the rounded beak-shaped protrusion (12) is identified, in 1-B: a perspective view is shown; in 1-C a side view from the side of the grip zone is shown, in 1-D a section with an enlargement of the height of the lips is shown, in 1-E a sectional view at the height of the beak is shown, in 1-F a bottom view of the alternative menstrual cup is shown, where preferred measurements and angles are identified.

The anatomical menstrual cup is a reusable product to collect menstruation.

The purpose of the present invention is the provision of an anatomical menstrual cup (10) containing in the lower part (resulting from the intersection of an elliptic paraboloid of revolution with two symmetrical convex surfaces (13, 14) around an vertical X axis (20)) a rounded beak-shaped protrusion (12) with two symmetrical convex grip zones (13, 14), which facilitate the insertion and extraction of the menstrual cup in the vagina.

The grip zones (13, 14) are symmetrically located with respect to the vertical X axis (20) that passes through the center of the menstrual cup.

Each of the grip zones contains a lip (15, 16) that allows pinching with the fingers of the woman who uses the anatomical menstrual cup to facilitate grip and removal.

Each lip has a height (17) to generate the necessary grip. This height is approximately equal to half the thickness of the wall of the anatomical menstrual cup in the zone where each lip (15, 16) is located.

Figure 2:
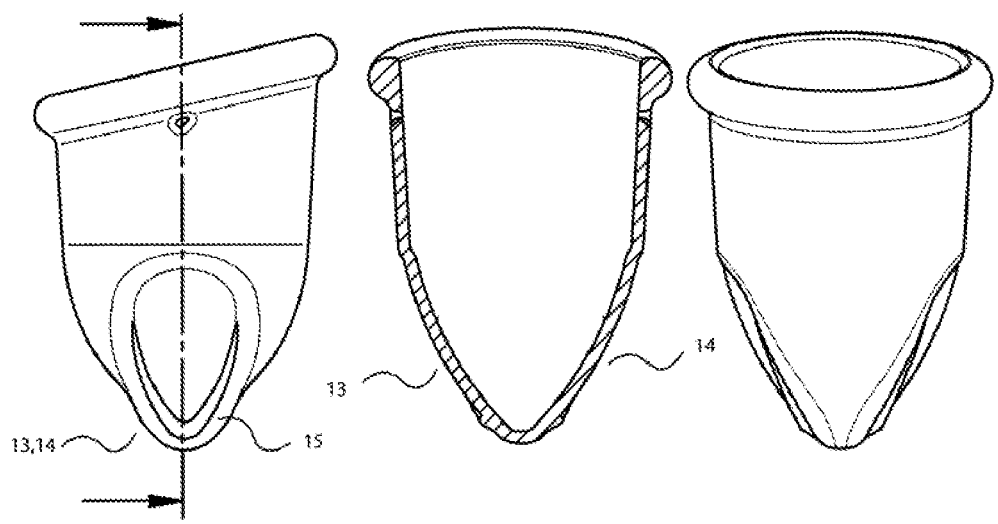
FIG. 2: Shows the two alternatives of the anatomical menstrual cup of the invention where the upper part of the grip zones (13, 14) is below the middle of the anatomical menstrual cup and where the upper part of the grip zones (13, 14) is located above the middle of the anatomical menstrual cup.
Figure 2:
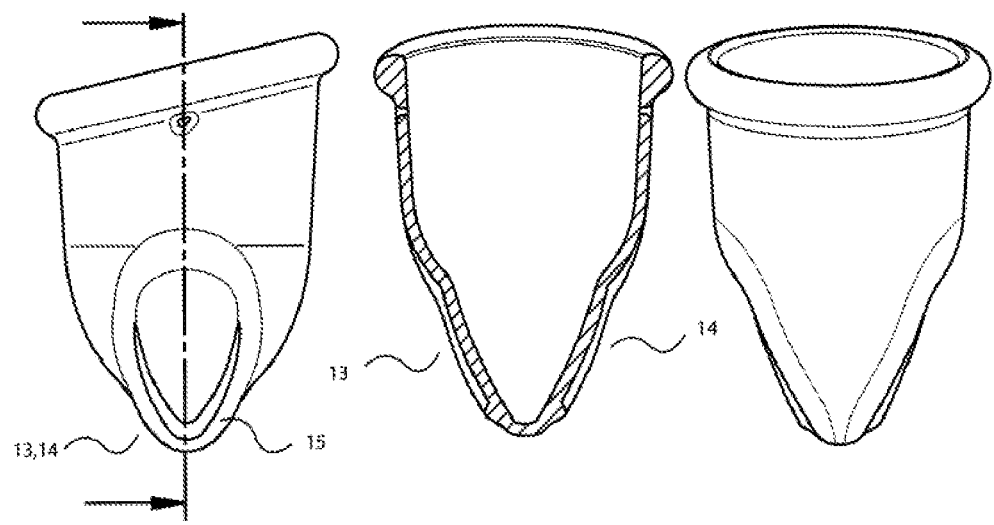

Among the variants of the anatomical menstrual cup (10), the upper part of the grip zones (13, 14) is below the middle of the anatomical menstrual cup (10), that is, below the horizontal Y axis (21) (see FIG. 2, alternative 1) or the upper part of the grip zones (13, 14) barely exceeds the middle of the anatomical menstrual cup (10), that is, it barely exceeds the horizontal Y axis (21) (see FIG. 2, alternative 2).

In one of the variants of the invention, the distance that the upper part of the grip zones (13, 14) exceeds the horizontal Y axis (21) is approximately equal to the thickness of the wall that makes up the anatomical menstrual cup (10).

In another variant of the invention, the distance below the upper part of the grip zones (13, 14) of the horizontal Y axis (21) is approximately equal to the thickness of the wall that makes up the anatomical menstrual cup (10).

The anatomical menstrual cup (10) contains an upper ring (18) that allows the cup to seal against the vaginal walls in order to avoid the loss of vaginal discharge when it is being used.

The upper ring (18) is not perpendicular to the X axis (20), which facilitates the insertion and extraction of the menstrual cup (10) in the vagina.

Figure 3:
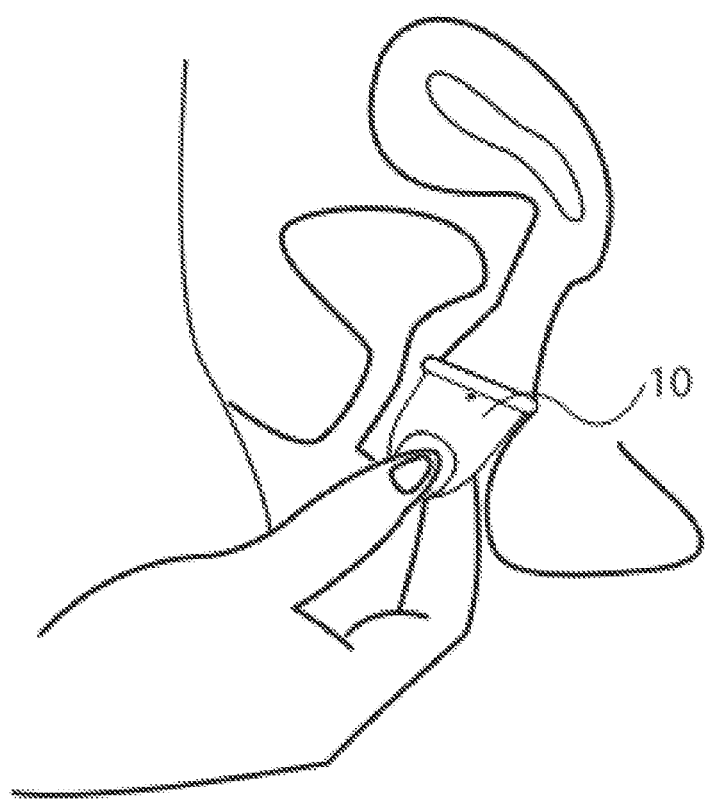
FIG. 3: Shows how the anatomical menstrual cup of the invention is placed in the user's vagina.

When the anatomical menstrual cup (10) is inserted into the vagina, the upper ring (18) is the first zone of the menstrual cup (10) that enters (see FIG. 3).

The anatomical menstrual cup (10) contains a pair of holes (19) that allow the insertion of an air flow at the moment of extraction, compensating the internal pressure with the external pressure and thus avoiding creating annoying pain.

Its hollow shape allows the collection of menstruation within it.

The anatomical menstrual cup (10) is inserted into the vagina for a time to collect the menstruation, then it is removed to empty it so that it can be used again. The anatomical menstrual cup (10) is made of an elastomer with the ability to be resilient, to deform and return to its original shape over and over again.

Among the preferred elastomer materials for the anatomical menstrual cup (10) thermoplastic elastomers or silicones are considered.

The material used to manufacture the anatomical menstrual cup (10) is TPE or medical grade silicone or any other medical grade material that meets these conditions. In particular, the anatomical menstrual cup (10) is produced by TPE injection.

The anatomical menstrual cup (10) has the ability to be folded so that it is small in size and allows a comfortable insertion into the vagina.

As the upper ring (18) is inclined, it allows to have a smaller contact area when it is folded inwards, resulting in a comfortable insertion into the vagina. This inclination is given by the angle δ that is within the range of 95° and 111° with respect to the vertical X axis (20) (see FIG. 1A).

When the anatomical menstrual cup (10) is folded to be inserted into the vagina, it exerts a force to return to its original position due to the elastomeric material that makes it up.

Once inside the vagina, the anatomical menstrual cup (10) unfolds into position for use (see FIG. 3).

To facilitate the deployment of the anatomical menstrual cup (10), it can be held by the grip zones (13, 14) and rotated with respect to the vertical X axis (20).

In this way, the anatomical menstrual cup (10) fits totally inside the vaginal cavity to collect the menstruation without leaks so that it is comfortable.

To extract the anatomical menstrual cup (10), the lower part (11) must first be grasped, pressing on the grip zones (13, 14), preferably with the index and thumb fingers; then the anatomical menstrual cup (10) is pulled out. To facilitate removal, the cup can be rotated about the vertical X axis (20) and then pulled out.

The lower zone (11) of the anatomical menstrual cup (10) has a rounded beak-shaped protrusion (12) with height that allows it to deform when pressed by the user with her fingers, generally thumb and index fingers, when she exerts pressure on symmetrical convex grip zones (13, 14). Cups generally have a stem at the bottom for pulling and removing the cup. However, pulling the stem can create a vacuum effect resulting in aches and pains. Said protrusion eliminates the need for a stem to remove it. Once the grip zones (13, 14) are pressed, the air comes out through the holes (19) allowing extraction without discomfort. At the same time, it results in greater wearing comfort due to the fact that the height of the cup decreases compared to those cups that have a stem and, given its rounded shape, guarantees comfort during use. The rounded shape of the beak, without edges, is decisive so that it cannot puncture or press on the inner walls of the vagina causing discomfort.

The convex grip zones are symmetrical with respect to the vertical X axis (20) allowing the user to hold the menstrual cup (10) with the fingers. The angle (α), between the grip surface and the vertical X axis (20), is within the range of 20° and 35° (see FIG. 1-D) and allows space between the cup and the vaginal walls, facilitating the user to place her fingers in the grip zones and remove the cup easily. The distance (B) (see FIG. 1-D) between both grip zones (13, 14) allows the deformation of the lower zone (11). The distance (B) is within the range of 6 mm and 17 mm.

The grip zones (13, 14) are convex to provide a greater interior volume and therefore greater capacity to collect menstruation fluid.

The lips (15, 16) that are inscribed in the grip zones (13, 14), have a thickness (17) with respect to the outer surface of the grip zones (13, 14) that prevent the fingers from slipping over the grip zones. The angle β, (see FIG. 1-D), between the outer surface of the grip zones (13, 14) and the upper surface of the lips (15, 16) is within the range of 60° and 150°. The angle β, ensures that the fingers are not displaced when the anatomical menstrual cup is removed from the vagina.

The lips (15, 16) that are inscribed in the grip zones (13, 14) have a "V" or "U" shape formed by the angle γ (see FIG. 1-F). The angle γ is within the range of 0° and 70°. The height "D" (see FIG. 1-F), prevents the fingers from slipping when pressing the grip zones (13, 14) and then rotating the menstrual cup (10) with respect to the vertical axis (20).

The lips (15, 16) that are inscribed in the grip zones (13, 14) have a height (17) to generate the necessary grip. This height is approximately equal to half the thickness of the wall of the anatomical menstrual cup in the zone where each lip is located (15, 16) and prevents slipping between the fingers when pressing the grip zones (13, 14).

The upper ring (18) allows the anatomical menstrual cup (10) to be sealed against the vaginal walls. The stiffness of the upper ring (18) is given by its thickness and its height in relation to the outside diameter and the height, ensuring the seal.

The upper ring (18) is not perpendicular to the vertical X axis (20) but forms an angle δ which is within the range of 95° and 111° (see FIG. 1-A). When the anatomical menstrual cup (10) is folded, said angle δ allows the resulting shape to be smaller than if the upper ring (18) were perpendicular.

The upper ring (18) has a rounded shape, without edges, which avoids discomfort inside the vagina.

Under the upper ring (18) are located at least two holes (19) that allow the passage of air when the menstrual cup (10) is being extracted from the vagina, avoiding an annoying suction sensation in the vagina.

The invention claimed is:

1. An anatomical menstrual cup comprising a lower part and an upper part separated by a horizontal Y axis, where the lower part results from the intersection of an elliptic paraboloid of revolution with two symmetrical convex surfaces around a vertical X axis, with a beak-shaped protrusion, with two symmetrical convex grip zones, which are configured to facilitate the insertion and removal of the menstrual cup into and from the user's vagina.

2. The anatomical menstrual cup according to claim 1, wherein each of the two symmetrical convex grip zones has a lip configured to allow the symmetrical convex grip zone to be pinched with the user's fingers to facilitate the extraction of said anatomical menstrual cup, in turn, the lower zone of the anatomical menstrual cup, has a beak-shaped protrusion with height configured to allow the beak-shaped protrusion to deform when being pressed by the user with her fingers, when she exerts pressure on the symmetrical convex grip zones, where said protrusion improves comfort of the user during use.

3. The anatomical menstrual cup according to claim 2, wherein in the grip zones that have a lip, the upper part of the grip zones is below the middle of the anatomical menstrual cup as below the horizontal Y axis or the upper part of the grip zones is substantially adjacent to the middle of the anatomical menstrual cup as substantially adjacent to the horizontal Y axis.

4. The anatomical menstrual cup according to claim 3, wherein the upper part of the grip zones is substantially adjacent to the middle of the anatomical menstrual cup as below the horizontal Y axis in a distance approximately equal to the thickness of the wall that makes up the anatomical menstrual cup.

5. The anatomical menstrual cup according to claim 3, wherein the upper part of the grip zones is substantially adjacent to the middle of the anatomical menstrual cup as substantially adjacent to the horizontal Y axis in a distance approximately equal to the thickness of the wall that makes up the anatomical menstrual cup.

6. The anatomical menstrual cup according to claim 1, further comprising an upper ring at the beginning of the upper part configured to allow the cup to seal against the vaginal walls of the user in order to avoid the loss of vaginal discharge when the anatomical menstrual cup is being used.

7. The anatomical menstrual cup according to claim 1, wherein the upper ring is not perpendicular to the vertical X axis as forming an angle d that is within the range of 95° and 111° when the anatomical menstrual cup is folded, said angle d is configured to allow the resulting shape to be smaller than if the upper ring were perpendicular.

8. The anatomical menstrual cup according to claim 1, wherein under the upper ring in the upper part there are at least two holes configured to allow the passage of the air when the menstrual cup is being withdrawn from the user's vagina.

9. The anatomical menstrual cup according to claim 2, further comprising an upper ring at the beginning of the upper part configured to allow the cup to seal against the vaginal walls of the user in order to avoid the loss of vaginal discharge when the anatomical menstrual cup is being used.

10. The anatomical menstrual cup according to claim 3, further comprising an upper ring at the beginning of the upper part configured to allow the cup to seal against the vaginal walls of the user in order to avoid the loss of vaginal discharge when the anatomical menstrual cup is being used.

11. The anatomical menstrual cup according to claim 4, further comprising an upper ring at the beginning of the upper part configured to allow the cup to seal against the vaginal walls of the user in order to avoid the loss of vaginal discharge when the anatomical menstrual cup is being used.

12. The anatomical menstrual cup according to claim 5, further comprising an upper ring at the beginning of the upper part configured to allow the cup to seal against the vaginal walls of the user in order to avoid the loss of vaginal discharge when the anatomical menstrual cup is being used.

13. The anatomical menstrual cup according to claim 2, wherein the upper ring is not perpendicular to the vertical X axis as forming an angle d that is within the range of 95° and 111° when the anatomical menstrual cup is folded, said angle d is configured to allow the resulting shape to be smaller than if the upper ring were perpendicular.

14. The anatomical menstrual cup according to claim 3, wherein the upper ring is not perpendicular to the vertical X axis as forming an angle d that is within the range of 95° and 111° when the anatomical menstrual cup is folded, said angle d is configured to allow the resulting shape to be smaller than if the upper ring were perpendicular.

15. The anatomical menstrual cup according to claim 4, wherein the upper ring is not perpendicular to the vertical X axis as forming an angle d that is within the range of 95° and 111° when the anatomical menstrual cup is folded, said angle d is configured to allow the resulting shape to be smaller than if the upper ring were perpendicular.

16. The anatomical menstrual cup according to claim 5, wherein the upper ring is not perpendicular to the vertical X axis as forming an angle d that is within the range of 95° and 111° when the anatomical menstrual cup is folded, said angle d is configured to allow the resulting shape to be smaller than if the upper ring were perpendicular.

17. The anatomical menstrual cup according to claim 6, wherein the upper ring is not perpendicular to the vertical X axis as forming an angle d that is within the range of 95° and 111° when the anatomical menstrual cup is folded, said angle d is configured to allow the resulting shape to be smaller than if the upper ring were perpendicular.

18. The anatomical menstrual cup according to claim 2, wherein under the upper ring in the upper part there are at least two holes configured to allow the passage of the air when the menstrual cup is being withdrawn from the user's vagina.

19. The anatomical menstrual cup according to claim 3, wherein under the upper ring in the upper part there are at least two holes configured to allow the passage of the air when the menstrual cup is being withdrawn from the user's vagina.

20. The anatomical menstrual cup according to claim 4, wherein under the upper ring in the upper part there are at least two holes configured to allow the passage of the air when the menstrual cup is being withdrawn from the user's vagina.

\* \* \* \* \*